United States Patent
Lovell et al.

(10) Patent No.: US 7,299,679 B2
(45) Date of Patent: Nov. 27, 2007

(54) STROBE DESORPTION METHOD FOR HIGH BOILING POINT MATERIALS

(75) Inventors: John Stanley Lovell, Arvada, CO (US); Patrick D. French, Aurora, CO (US); Anthony René Barringer, Golden, CO (US)

(73) Assignee: ADA Technologies, Inc., Littleton, CO (US)

( * ) Notice: Subject to any disclaimer, the term of this patent is extended or adjusted under 35 U.S.C. 154(b) by 0 days.

(21) Appl. No.: 11/081,006

(22) Filed: Mar. 14, 2005

(65) Prior Publication Data

US 2005/0235739 A1      Oct. 27, 2005

Related U.S. Application Data

(63) Continuation of application No. 10/719,840, filed on Nov. 21, 2003, now Pat. No. 6,895,804.

(60) Provisional application No. 60/472,386, filed on May 20, 2003, provisional application No. 60/428,531, filed on Nov. 21, 2002.

(51) Int. Cl.
   G01N 1/22    (2006.01)
   G01N 1/24    (2006.01)
(52) U.S. Cl. ............... 73/31.05; 73/863.11; 73/863.12; 73/863.21; 73/863.71; 73/863.813
(58) Field of Classification Search ...... 73/23.2–31.07, 73/863.11, 863.21, 863.51, 863.71, 864.81, 73/864.84

See application file for complete search history.

(56) References Cited

U.S. PATENT DOCUMENTS

| | | | |
|---|---|---|---|
| 3,748,905 | A | 7/1973 | Fletcher et al. |
| 4,580,440 | A | 4/1986 | Reid et al. |
| 4,718,268 | A | 1/1988 | Reid et al. |
| 4,754,655 | A | 7/1988 | Parker et al. |
| 4,819,477 | A | 4/1989 | Fisher et al. |
| 4,820,920 | A | 4/1989 | Bather |
| 4,867,796 | A | 9/1989 | Asmus et al. |
| 5,092,155 | A | 3/1992 | Rounbehler et al. |

(Continued)

FOREIGN PATENT DOCUMENTS

WO      WO-9427145 A1      11/1994

OTHER PUBLICATIONS

Fryer et al., "Dependence of the Glass Transition Temperature of Polymer Films on Interfacial Energy and Thickness," 2001, Macromolecules, vol. 37, No. 16, pp. 5627-5634.

(Continued)

*Primary Examiner*—Hezron Williams
*Assistant Examiner*—David A. Rogers
(74) *Attorney, Agent, or Firm*—Sheridan Ross P.C.

(57) ABSTRACT

The invention is directed to a system and method for detecting substances, such as high boiling and low vapor pressure materials, using high energy radiation imparted by a suitable radiation source, such as a strobe or laser over a short time period. The radiation source causes the materials to vaporize. A system handling system is used in conjunction with a detector to detect the presence of the materials including explosives, explosive-related compounds, chemical warfare agents, drugs, toxic industrial compounds, and derivatives thereof.

22 Claims, 12 Drawing Sheets

U.S. PATENT DOCUMENTS

Figure 2:
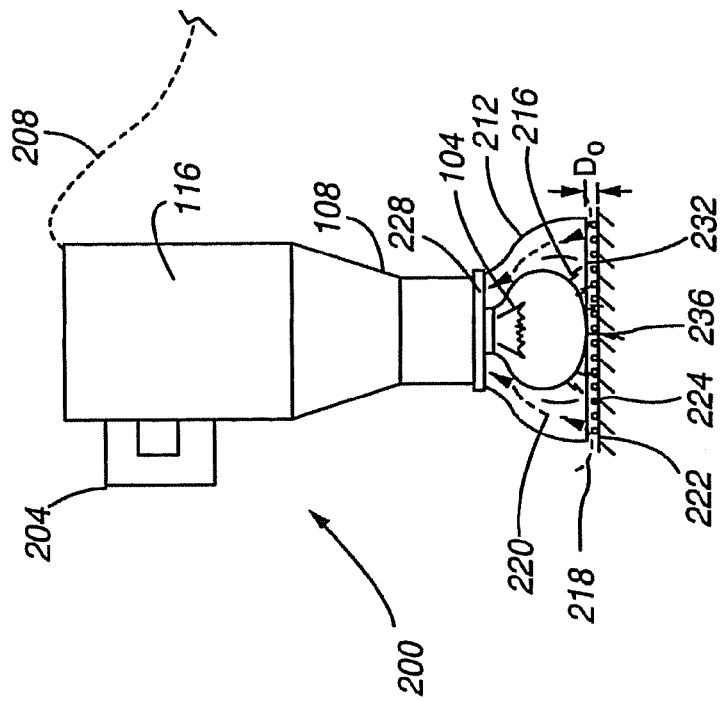

| | | | |
|---|---|---|---|
| 5,122,127 A | | 6/1992 | Stanley |
| 5,138,889 A | | 8/1992 | Conrad |
| 5,278,418 A | | 1/1994 | Broadhurst |
| 5,476,794 A | | 12/1995 | O'Brien et al. |
| 5,585,575 A | | 12/1996 | Corrigan et al. |
| 5,663,561 A | * | 9/1997 | Franzen et al. ............. 250/288 |
| 5,751,897 A | | 5/1998 | Van Alstyne |
| 5,842,995 A | | 12/1998 | Mahadevan-Jansen et al. |
| 5,859,375 A | | 1/1999 | Danylewych-May et al. |
| 5,862,273 A | | 1/1999 | Pelletier |
| 5,904,900 A | | 5/1999 | Bleuse et al. |
| 5,942,699 A | | 8/1999 | Ornath et al. |
| 5,965,884 A | * | 10/1999 | Laiko et al. ................. 250/288 |
| 6,085,601 A | | 7/2000 | Linker et al. |
| 6,353,476 B1 | | 3/2002 | Allen et al. |
| 6,446,514 B1 | | 9/2002 | Danylewych-May et al. |
| 6,477,907 B1 | | 11/2002 | Chambers et al. |
| 6,558,626 B1 | | 5/2003 | Aker et al. |
| 6,558,956 B1 | | 5/2003 | Carron et al. |
| 6,621,574 B1 | | 9/2003 | Forney et al. |
| 6,692,694 B1 | | 2/2004 | Curry et al. |
| 6,734,423 B2 | * | 5/2004 | Bryden ....................... 250/288 |
| 6,797,242 B2 | | 9/2004 | Neumann et al. |
| 6,828,795 B2 | | 12/2004 | Krasnobaev et al. |
| 6,838,663 B2 | * | 1/2005 | Coon et al. ................. 250/288 |
| 6,897,951 B2 | | 5/2005 | Womble et al. |
| 7,098,672 B2 | | 8/2006 | Belyakov et al. |
| 2003/0039299 A1 | | 2/2003 | Horovitz et al. |
| 2003/0155504 A1 | * | 8/2003 | Motchkine et al. ......... 250/287 |
| 2003/0230152 A1 | | 12/2003 | McGrill et al. |
| 2005/0248758 A1 | | 11/2005 | Carron et al. |
| 2007/0056388 A1 | | 3/2007 | Henry et al. |

OTHER PUBLICATIONS

"2,4-Dinitrotoluene Material Safety Data Sheet," Sep. 1997, Toxic Air Contaminant Identification Series, pp. 437-439.

Lewis, J., "Recommendation to List 2,4,6-Trinitrotoluene (TNT) as a Potential Pollutant," Apr. 2001, pp. 1-8.

PCT—Notification of Transmittal of The International Search Report and the PCT International Search Report dated Jun. 22, 2004.

Paul Tompkins et al.; "Icebreaker: An Exploration of the Lunar South Pole," copyright 1999 by the Space Studies Institute, 11 pages.

V.A. Morosov et al.; "2πspectrometer: A new apparatus for the investigation of ion surface interaction," Rev. Sci. Instrum. 67(6) (Jun. 1996), pp. 2163-2170.

Yvan Simard et al.; "New technology for the detection of micronekton: multivariate acoustics, sampling and data analysis strategies," printed Oct. 13, 2003, 24-pages, available at http://pulson.seos.uvic.ca/meeting/scor2000/simard/simard.html.

V. Debur et al.; "Position-sensitive detector for the 6-meter optical telescope," printed Nov. 13, 2003, 6 pages, available at http://arxiv.org/pdf/astro-ph/0310353.

K. Fransson; "The Trigger System of the CELSIUS/WASA Detector," Physica Scripta T99, (2002), pp. 176-182.

M. Mayer et al.; "Performance of the CdZnTe Strip Detectors as Sub-millimeter Resolution Imaging Gamma Radiation Spectrometers," undated, 5 pages.

* cited by examiner

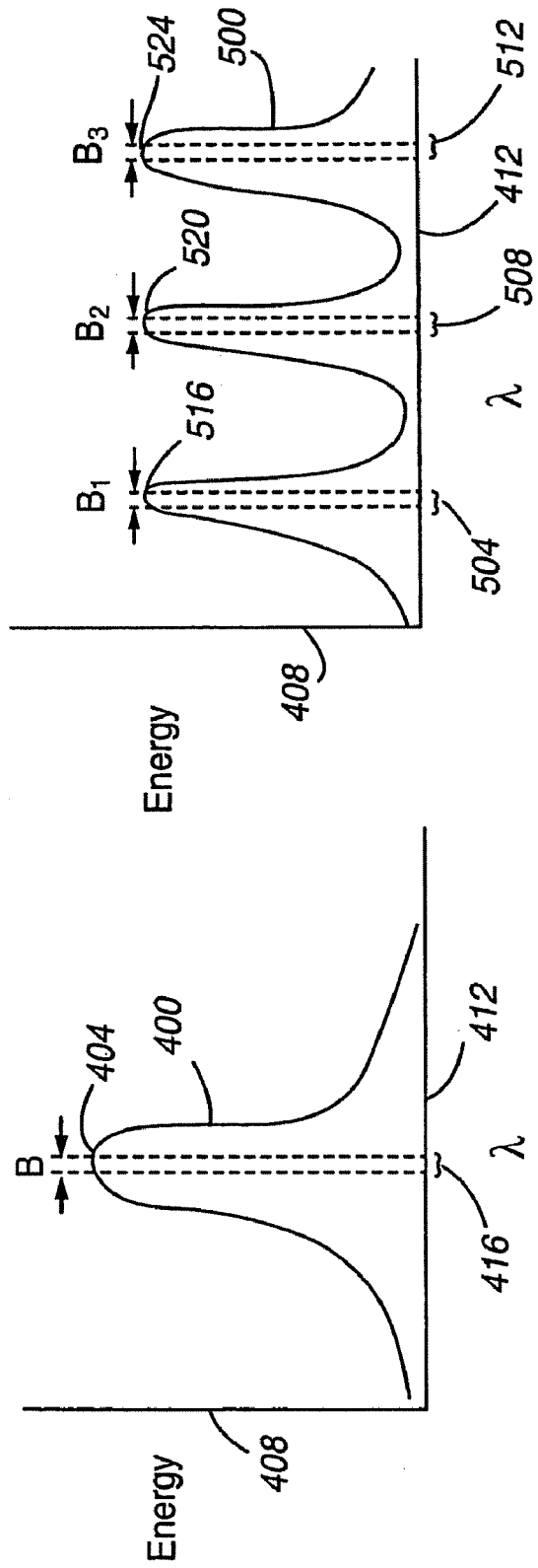

STROBE DESORPTION METHOD FOR HIGH BOILING POINT MATERIALS

CROSS REFERENCE TO RELATED APPLICATIONS

The present application is a continuation of U.S. patent application Ser. No. 10/719,840 filed Nov. 21, 2003 now U.S. Pat. No. 6,895,804 entitled "STROBE DESORPTION METHOD FOR HIGH BOILING POINT MATERIALS", which claims the benefits of U.S. Provisional Application Ser. Nos. 60/428,531, filed Nov. 21, 2002, and 60/472,386, filed May 20, 2003, to Lovell, et al., each of which is incorporated herein by reference in its entirety.

STATEMENT REGARDING FEDERALLY SPONSORED RESEARCH OR DEVELOPMENT

The U.S. Government has a paid-up license in this invention and the right in limited circumstances to require the patent owner to license others on reasonable terms as provided for by the terms of Contract No. DAAD17-03-C-0064 awarded by the U.S. Department of the Army.

FIELD OF THE INVENTION

The present invention is directed generally to the detection of materials and specifically to the detection of materials using high energy radiation.

BACKGROUND OF THE INVENTION

There are estimated to be over 120 million land mines distributed throughout the world in 65 countries. Each year, thousands of noncombatants, a large proportion of which are children, are injured or killed by unexploded land mines. Although clearing efforts are under way, the International Red Cross, estimates that, at the present rate of clearance, it will take over 1,100 years and cost over $33 billion (in today's dollars) to clear the currently deployed mines.

The current mine detection technology is partly responsible for the slow mine clearance rate. Currently, deminers and dismounted countermine engineers use metal detectors. Although this somewhat primitive technique is effective for metal housed land mines, many modern land mines are not metal housed and contain a low metal content, which can severely limit the effectiveness of metal detectors. Such mines must be located by "probing" with probes.

"Probing" can be an extremely dangerous and time-consuming method of detecting land mines. This method involves "feeling" for mines by methodically inserting rigid rods into the soil. When a solid object is encountered in the soil, it is then excavated to determine if the object is a mine.

Another mine detection technique is infrared or IR mine detection. Such systems rely on the fact that mines have a different thermal mass than their surroundings and therefore heat up and cool down at different rates. Furthermore, the disturbance in the soil from the burial changes the porosity of the soils, resulting in anomalous water content and a different heating and cooling response to diurnal changes. IR systems are most promising as a support for other technologies, rather than as a stand alone technique. IR sensors are readily available as imaging systems and, when combined with neural networks, can detect individual mines as hot or cold spots on the surface of the ground.

Ground penetrating radar (GPR) is a method of directly imaging buried objects. GPR uses a wideband antenna to irradiate the soil with an electromagnetic field covering a large frequency range. Reflections from the soil caused by dielectric variations are measured and converted into an image. Although promising, this technology has limitations, in particular the resolution required to image small objects requires GHz frequencies which decrease soil penetration and increase image clutter. The high cost of GPR systems also inhibits widespread applications in mine clearing operations.

Other mine detection techniques seek to locate mines by detecting trace levels of explosives in the soil around the buried mines. Because mines are typically of cheap construction and not hermetically sealed, mines buried for long periods can "leak" explosives and derivates thereof into the soil surrounding the buried mine. In time, the concentrations in the surrounding soil can increase to 2-8 ppb w/w for TriNitro Toluene or TNT, the explosive used in over 85% of all land mines. TNT contaminants, such as 2,4-dinitrotoluene and TNT derivatives, such as 2-amino-4,6-dintrotoluene or 2-ADNT and 4-amino-2,6-dintrotoluene or 4-ADNT, may be present at concentrations an order of magnitude greater or more than the primary explosive. Evapo-transpiration in soils can move the leaked explosives and explosive related chemicals to the surface, where the surface microlayer of the soils potentially adsorbs and concentrates the vapors, particularly when the surface dries. The surface microlayer refers to the top millimeter or two of the soil at the soil/atmosphere interface.

Canines are an example of a detection method based on the presence of trace levels of explosives in the surface microlayer around the mine and have been used for land mine detection for decades. Experiments have shown that canines smell the explosives that leak from most types of land mines. Even though canines can be effective for this purpose, their use is not without problems. Logistical problems are significant, and dogs are expensive to train and maintain. Dogs do not perform well under all field conditions. In addition, the performance of the dog can be limited by the skill of the dog handler, the dog's desire to work, and the health of the dog.

Currently, various systems are under development to detect land mines by "sniffing" above the soil for the ultra-trace explosive vapors. This technique can be quite challenging as the equilibrium concentration of the ultra-trace explosive vapors in the soil/atmosphere boundary layer is typically quite low and therefore only minute quantities ($10^{-16}$-$10^{-12}$ g) are available for detection. The amount of material that is available to passive vapor sensing systems is limited to no more than the vapor in equilibrium with the explosive related chemicals (ERCs) distributed in the surface soils over and near the land mine. Examples of ERC's include explosive co-contaminants such as isomers of dinitrotoluene and degradation products of the explosives, such as 2-amino 4,6 dinitrotoluene and 4-amino 2,6-dinitrotoluene. Unfortunately, TNT is a solid with a very low vapor pressure under ambient conditions. The TNT, and many other explosives, are crystalline solids and have high boiling points. TNT, for instance, boils with decomposition at about 255° C. Worse, explosives and explosive derivatives (explosive related chemicals or ERCs) aggressively bind to surfaces and soils. The distribution of explosives and ERCs in the soil can be quite heterogeneous. The low equilibrium vapor pressure of TNT in the soil/atmosphere boundary layer and the limited volume of the boundary layer air imply that passive chemical vapor sensing systems require sensitivities in the picogram range or even lower. This can be difficult to implement as the passive chemical sensing system must separate the signal from a highly variable background.

In addition to land mines, explosives and other controlled substances, such as drugs, have become major societal problems. Increasingly, terrorist acts using explosives are becoming a problem not only for countries in the Middle East but also for Western countries in other parts of the world. Drug abuse has been a longstanding problem for Western countries and consumes large amount of law enforcement resources each year. As in the case of land mines, canines, metal detectors, and "sniffer" detectors have been used at various locations, such as airports, border crossings, and the like to detect explosive devices and illegal drugs. These measures have had mixed success for many of the same reasons as their limited successes in detecting land mines.

Another measure that has been employed to detect contraband substances has been to collect loose particles from surfaces or skin with a vacuum cleaner or a swipe. The swipe or the particles collected by the vacuum are then heated to release the vaporizable material for analysis. This approach is in routine use at airports throughout the world for screening airline passengers. An example of such a system is the Barringer™ Ion Scan System™. This technique has drawbacks. The use of swipes or particle vacuums is an intermittent process, which requires manual intervention between the sampling and analysis. This is a time consuming approach that is inherently slow.

SUMMARY OF THE INVENTION

These and other needs are addressed by the various embodiments and configurations of the present invention. The present invention is directed to a system and method for detecting substances, such as high boiling point and low vapor pressure materials, using high energy radiation imparted by a suitable radiation source, such as a strobe or laser, over a short time period. Examples of substances that are detectable include explosives and other controlled substances, such as drugs. "Explosives" refer to a chemical compound, usually containing nitrogen, that detonate or deflagrate as a result of shock or heat. "Detonation" refers to a rapid, self-propagating decomposition of an explosive accompanied by a high-pressure-temperature wave that moves at about 1000 to about 9000 meters/second. "Deflagration" refers to a rapid autocombustion of particles of explosive as a surface phenomenon. "Drugs" refer to a substance that acts on the central nervous system, e.g., a narcotic, hallucinogen, barbiturate, or psychotropic drug.

In one embodiment, a method for detecting a high boiling point and/or a low vapor pressure material is provided that includes the steps of:

(a) directing radiation from a radiation source onto a surface potentially comprising a high boiling point and/or low vapor pressure material, wherein, during a time interval of no more than about $1/1000^{th}$ seconds, the directed radiation has a cumulative or aggregate energy of at least about 1,200 Joules;

(b) collecting an airborne sample at and/or near the surface (e.g., soil, clothing, travel documents, luggage, skin, metal, glass, plastic, painted surfaces, and vegetation); and (c) detecting whether or not the high boiling point and/or low vapor pressure material is present in the collected sample.

This embodiment of the present invention can greatly increase the concentration of low-vapor pressure material in the air and facilitate their detection, thereby providing a detection system of high accuracy and sensitivity. It has been shown that the use of a strobe as the radiation source can amplify the detection signal from trace explosives in the soil by two or three orders of magnitude more than the detection signal generated by the trace explosives at equilibrium vapor pressure in the boundary layer between the soil and overlying atmosphere. This signal amplification can provide a commensurate improvement in the detection limits of the system. This increase in detection limit can in turn increase the efficiency and improve the confidence of demining exercises. While not wishing to be bound by any theory, it is believed that the energy emitted by the radiation source is high enough to cause desorption of the high boiling point and/or low vapor pressure target material(s) and/or some other material(s), such as water and micro-particles, that carry the target material into the air, which is then collected by the sample collection system The amount of energy can be sufficient to volatilize vaporizable materials, including the ubiquitous water layer that is closely bound to virtually all surfaces and particles. The volatilization of the water facilitates the creation of a plume and carries the condensed traces of target materials, such as explosives and drugs, into the ambient or surrounding air. The sudden influx of energy can create a plume of heated air at the surface that will lift micro-particles from the surface. The very brief time interval of the energy emission can ensure that all of the energy is only absorbed into the immediate surface of the substrate, with very little being used to heat the bulk of the material.

The radiation source can be any emitter capable of providing radiation satisfying either (i) and/or (ii). Examples of suitable sources include a strobe and a laser.

The high boiling point and/or low vapor pressure material can be any suitable material. Examples include explosives, drugs, particulates, metal-bearing particulates, chemical warfare agents and low vapor pressure toxic industrial compounds, and derivatives thereof. A boiling point material has a boiling point of at least about 150° C. A low vapor pressure material has a vapor pressure of no more than about $2 \times 10^{-3}$ mm Hg under standard temperature and pressure.

A volatilizing agent can be applied to the surface before radiation emission to enhance detection efficiency and accuracy. The volatilizing agent is believed to become airborne or vaporize when contacted by the emitted radiation and assist in capturing and transporting high boiling point and/or low vapor pressure materials to the sample handling, analytical, or collection system. The volatilizing agent can be for example water, water vapor, a volatile liquid such as alcohol, and mixtures thereof In high volume or sampling rate applications, the radiation source preferably can repeat the radiation emitting step (or provide a sample rate) at a frequency of at least about 1 Hz. Examples of high volume applications include land mine detection where each of a plurality of areas of a target zone must be tested and drug and/or explosive detection at border crossings, airports, and the like where a high volume of people and/or items must be checked.

To provide a higher energy efficiency and greater detection, the outputted energy profile of the radiation source can be configured to emphasize selected material absorption bands. Which band is emphasized depends on the collection mechanism(s) to be emphasized by the system For example, the peak of the energy profile can be located in a radiation absorption band of the (target) material to cause direct vaporization of the material. In another example, the peak of the profile is located in a radiation absorption band of the volatilizing agent to cause vaporization of the agent as a carrier of the vapor phase target material(s).

To maintain the integrity of the collected sample, it can be important to prevent the target material(s) from collecting on a surface of the sample handling system. Typically, the collected sample is transported to the detector through a heated conduit. The heated conduit is preferably at a temperature that prevents condensation and/or absorption of the target material on the surface of the conduit. Moreover, the internal surface of the conduit can be modified to render the surface non-polar and less likely to provide binding sites for the low vapor pressure target materials. An example of a modification process is silanization and subsequent methylation of the surface to eliminate polar absorption sites.

The detection system can include a housing surrounding the radiation source and inlet into the sample handling system to reflect radiation towards the sample-containing surface and contain the airborne sample. Preferably, the offset distance between either a surface of the radiation source or a peripheral edge of the housing on the one hand and the surface on the other is no more than about 5 cm.

The methodology and system of the present invention can provide benefits relative to conventional systems.

First, the use of a large, virtually instantaneous delivery of energy can make otherwise difficult-to-detect materials detectable. High boiling point and low vapor pressure material, such as the vapors of explosives, chemical warfare agents, toxic chemicals, and narcotics, can leave the illuminated surface as an easily detected, sharply-defined plume as a vapor and/or as a condensate on airborne micro-particles. The method can be used to search for buried explosives, including land mines, screen cargo containers for contraband explosives and explosive devices, detect the explosives in the triggering mechanisms of nuclear weapons and contraband narcotics, and screen luggage, passengers, employees, and other persons entering secure or restricted facilities.

Second, the present invention can permit very fast screening, with a low false alarm rate and a high degree of confidence.

Third, the present invention can be hard to foil when the target material is being carried by the scanned object.

Fourth, the present invention can perform remote and automatic mine detection and thereby provide a safe and rapid method of detecting land mines.

Fifth, the present invention can be relatively inexpensive to manufacture and operate.

Sixth, the present invention can detect materials notwithstanding low equilibrium vapor pressures in the soil/atmosphere boundary layer and the limited volume of the boundary layer air without requiring sensitivities in the picogram range or even lower. In this manner, the system of the present invention can avoid the design problems of separating the signal from a highly variable background.

Seventh, the present invention can be continuous, rather than intermittent and avoid the need for manual intervention between the sampling and analysis.

These and other advantages will be apparent from the disclosure of the invention(s) contained herein.

The above-described embodiments and configurations are neither complete nor exhaustive. As will be appreciated, other embodiments of the invention are possible utilizing, alone or in combination, one or more of the features set forth above or described in detail below.

BRIEF DESCRIPTION OF THE DRAWINGS

FIG. 1 is an electrical flow schematic of a sensing system according to a first embodiment of the present invention;

FIG. 2 is a side view of a portable sensing system according to another embodiment of the present invention;

FIG. 3 is a side view of vehicle-mounted sensing system according to yet another embodiment of the present invention;

FIG. 4 is a plot of energy (vertical axis) versus radiation wavelength for a radiation source according to yet another embodiment of the present invention;

FIG. 5 is a plot of energy (vertical axis) versus radiation wavelength for a radiation source according to yet another embodiment of the present invention;

FIG. 6 is a test apparatus used in an experiment according to an embodiment of the present invention;

FIG. 7 is a plot of intensity (ion count) (vertical axis) versus scan number (horizontal axis) for an experiment using the apparatus of FIG. 6;

FIG. 8 is a test apparatus used in an experiment according to an embodiment of the present invention;

FIG. 9 is a plot of intensity (ion count) (vertical axis) versus scan number (horizontal axis) for an experiment using the apparatus of FIG. 8;

FIG. 10 is a plot of intensity (ion count) (vertical axis) versus scan number (horizontal axis) for an experiment using the apparatus of FIG. 8;

FIG. 11 is a side view of a sensing system according to a further embodiment of the present invention;

FIG. 12 is a plot of intensity (ion count) (vertical axis) versus scan number (horizontal axis) for an experiment using the test apparatus of FIG. 8;

FIG. 13 is a plot of intensity (ion count) (vertical axis) versus scan number (horizontal axis) for an experiment using the test apparatus of FIG. 8; and FIG. 14 is a plot of intensity (ion count) (vertical axis) versus scan number (horizontal axis) for an experiment using the test apparatus of FIG. 8.

DETAILED DESCRIPTION

An embodiment of the detection system of the present invention is depicted in FIG. 1. The detection system 100 includes a radiation source 104, a power source 108, a sample handling system 112, a detector 116, a volatilizing agent applicator 120, a controller 124, and a user interface 128. The detection system 100 illuminates a sample area with radiation emitted by the radiation source 104, transports a sample collected at or near the sample area using the sample handling system 112 to the detector 116, and measures the concentration of or otherwise detects the presence of one or more target substances using the detector 116. The sample contains volatilized materials, including the target material(s) to be detected if present.

The target material can be a semi-volatile co-contaminant or a high boiling point and/or low vapor pressure material or a derivative thereof. Typically, a high boiling point material has a boiling point of at least about 150° C., more typically of at least about 250° C. and a low vapor pressure material is a material having a vapor pressure of no more than about $2\times10^{-3}$ mm Hg and more typically of no more than about $2\times10^{-4}$ mm Hg under standard temperature and pressure (STP). The derivative can itself be a high boiling point and/or low vapor pressure material. Examples of TNT derivatives include 2-ADNT and 4-ADNT. Such derivatives can be unique markers to the presence of the source substance. Examples of target materials include explosives, such as TNT, nitroglycerine, ammonium nitrate, acetylides of copper and/or silver, mercury fulminate, lead azide, diazodinitrophenol, nitrosoguanidine, lead styphnate, cyclotrimethylenetrinatramine or RDX, pentaerythritol tetranitrate or PETN, dynamite, semtex, EGDN, DMNB, H-6, C-4, picric acid, nitrocellulose, and illicit drugs such as cocaine, heroin, opium, marijuana, methamphetamines, LSD, and co-contaminants from the manufacturer or purification of these drugs.

The sample area can be any suitable animate or inanimate surface. The typical surface for the detection of land mines maybe the overlying soil or vegetation. The method may also be applied to other surfaces for security applications in which case the sample area can be the skin of a body part, such as a hand, clothing, travel documents, luggage, metal, glass, plastic and painted surfaces, on vehicles or cargo containers, wood and canvas.

Referring again to FIG. 1, the radiation source 104 can be any suitable radiation emitter capable of emitting broadband radiation or radiation in one or more desired wavelength bands having a cumulative energy of at least about 200 Joules, more typically of at least about 1,200 Joules, and even more typically ranging from about 2,400 to about 4,800 Joules over a time period of no more than about $1/100^{th}$ seconds, and even more typically of no more than about $1/1000^{th}$ seconds. Although any range of radiation wavelengths that will be rapidly absorbed by the target and the underlying surface may be used, such as infrared and visible, the source 104 typically outputs energy in the wavelength range of from about 300 nm to about 700 nm in the visible wavelengths and 700 nm to 2 microns in the infrared region of the electromagnetic spectrum. Preferred radiation emitters include strobes and lasers. The source 104 typically is operable to emit radiation of the desired energy levels at a relatively high frequency of illumination cycles (or sample rates), typically of at least about 0.2 Hz, more typically of at least about 0.5 Hz, and even more typically of at least about 1 Hz. The preferred power source is a high-powered strobe, typically with a xenon flash tube as a light source or a laser with a suitable wavelength that couples with the target material, underlying surface or water on the underlying surface.

While not wishing to be bound by any theory, it is believed that the target substance and/or a derivative thereof is captured by the sample handling system 112 by one or more differing mechanisms. One possible mechanism is an increase in the vapor pressure of the target substance due to heating of the surface by the radiation source. Another possible mechanism is volatilization of the target substance. The amount of energy imparted to the target substance by the radiation source 104 is sufficiently high to heat the substance above its boiling temperature or boiling point if the substance is a liquid or above its sublimation temperature or sublimation point if the substance is a solid. A third possible mechanism is the displacement of small (micro) particulates from the sample area in response to the heat imparted by the radiation source 104. The target substance is located on the displaced particulates, which are removed as part of the sample. A fourth possible mechanism is the volatilization of a non-target substance, such as water, with the resulting vapor entraining the target substance and removing it from the surface of the sample area. Typically, soil includes a thin film of water molecules which, when illuminated by the radiation, will form a plume of water vapor that will carry the target substance to the sample handling system 112. The volatilization can be by a direct phase transition from the liquid to the gas phases or from the solid to the gas phases. Any of these mechanisms can be rendered more effective by the radiative heating of the air adjacent the sample area. The heated air will rise and can entrain any resulting vapors released by the sample area.

The radiation source 104 can be configured to emphasize one or more of these mechanisms. By way of example, the first mechanism, volatilization of the target substance, or the third mechanism, volatilization of a non-target substance (such as water or air), can be emphasized by designing the source 104 to output the higher energy levels in the radiation wavelength absorption band of the target or non-target substance. As will be appreciated, molecules absorb differing wavelengths of radiation to different degrees. Some wavelengths are only weakly absorbed or not absorbed at all by the molecule while other wavelengths are highly absorbed by the molecule. The wavelength band most absorbed by water, for instance, ranges from about 600 nm to about 2 µm.

FIGS. 4 and 5 illustrate energy output waveforms for the radiation source 104 according to differing invention configurations. FIG. 4 shows the energy output waveform 400 of the source 104 during an illumination cycle, with the vertical axis 408 being in Joules and the horizontal axis 412 being radiation wavelength in angstroms. The peak or average 404 of the waveform 400 is contained within the highest absorption band "B" 416 for the selected target or non-target substance. FIG. 5 illustrates the energy output waveform 500 for one or more sources 104. The waveform 500 has three peaks or averages, namely points 516, 520, and 524, contained within wavelength bands $B_1$, $B_2$, and $B_3$ 504, 508, and 512, respectively. The use of multiple wavelength bands can be used to impart energy simultaneously to a variety of target and non-target substances to thereby use several of the above mechanisms in a single illumination cycle. For example, the first band 504 could be a high absorption band for water, the second band 508 for TNT, and the third band 512 for particulates on the surface of the sample area.

The power source 108 can be any suitable power source producing sufficient pulsed energy to power the radiation source 104 at the desired frequency. For a strobe, the power source 108 typically includes one or more banks of capacitors with a second energy source, such as a generator, powering or energizing the capacitors.

The sampling handling system 112 typically includes a heated conduit (not shown) in communication with a vacuum pump (not shown). The vacuum pump maintains a suction or negative pressure (relative to ambient pressure) to draw the sample into the inlet of the conduit. The vacuum pump may be located on the conduit upstream or downstream of the detector 116. A heater (not shown) typically heats the conduit using a coiled arrangement, with the heating elements being coiled around the conduit. The heating elements can be electrical or configured to transport a heated medium, such as water. The temperature of the internal surface of the conduit is preferably maintained at a temperature high enough to prevent absorption of the target materials on the surface of the conduit. In an alternative configuration, the internal surface of the conduit is maintained at a temperature above the boiling point and/or sublimation point (or condensation temperature) of the target substance to prevent the substance from precipitating out or condensing onto the conduit. Typically, the temperature of the conduit is at least about 100° C. and more typically at least about 200° C. In an alternative configuration a plume containing particulates released from the sample area is passed through a filter designed to concentrate or collect the particulates. The filter is heated to release the low vapor pressure condensable target materials into the detection or analytical device. The filter may be heated continuously, or alternatively intermittently, to release the target material from particulates collected over a period of time, to improve the detection limit of the detection system. The conduit surface adjacent the sample is preferably nonpolar to further reduce the likelihood of the target substance from adhering to the conduit surface. In a preferred arrangement, the conduit is a glass and/or ceramic-lined stainless steel. The conduit may include a silanizing agent, such as dichlorodimethyl silane, to deactivate the conduit surface and provide an even lower likelihood of the target material collecting on the conduit surface.

The detector 116 can be any device or collection of devices capable of detecting the target substance(es). Suitable detectors include chemical detectors, spectrometers, and biosensors. Specific examples of detectors include fluorescence quenching polymer detectors such as the FIDO™ sensor produced by Nomadics™, ion mobility spectrometers, mass spectrometers, surface acoustic wave detectors, micro-cantilever detectors, artificial nose sensors, a gas chromatograph with an electron capture detector or ECD and a thermionic detector or TID detector, biosensors, Micro-Electro-Mechanical System or MEMS devices with a gas chromatograph with electron capture or thermionic detection, artificial noses (that rely on differential swelling of any array of polymers when certain types of vapors are absorbed), and quartz quart crystal microbalance sensors.

The volatilizing applicator 120 applies a volatilizing agent to the sample area before illumination of the area by the radiation source 104. The volatilizing agent is already a vapor or vaporizes, by boiling or sublimation, to produce a vapor plume. The plume entrains target substances and transports them to the inlet of the conduit. Examples of volatilizing agents include water and volatile organic solvents, such as ethanol. The applicator 120 is typically a pressurized spray-type apparatus and can include one or more nozzles positioned around the periphery of the radiation source 104. As will be appreciated, certain types of soils, such as soils in arid or semi-arid regions, can have little water present in the upper soil layer. The application of water to the sample area prior to illumination can enhance the effectiveness and sensitivity of the detection system.

The controller 124 is typically a microprocessor with volatile and/or nonvolatile memory. The controller receives and responds to feedback from various sensors, such as temperature sensors, voltage sensors, current sensors, and the like and commands from a user and issues appropriate control signals to system components. The controller further processes measurement signals received from the detector 116 and interfaces with the user interface 128 to provide the measurements in a selected format to a user. For example, the controller can apply calibration equations and scaling factors to convert signal magnitude into a measurement value and/or compare the signal magnitude and/or measurement value to predetermined thresholds to determine whether a target or non-target substance is present. The controller can also issue warning signals in the event of system malfunction.

The user interface 128 can be any suitable interface depending on the application. The interface 128 can provide audio and/or video feedback to the user. For example, the interface 128 can be an audio and/or visual alarm when a target material is detected, a display identifying substances detected and their concentrations, a warning light that is illuminated when a target material is detected, and any combination of the foregoing. The user interface can also include user controls, such as buttons, toggles, switches, keys, and the like to provide user commands to the controller 124.

Figure 1:
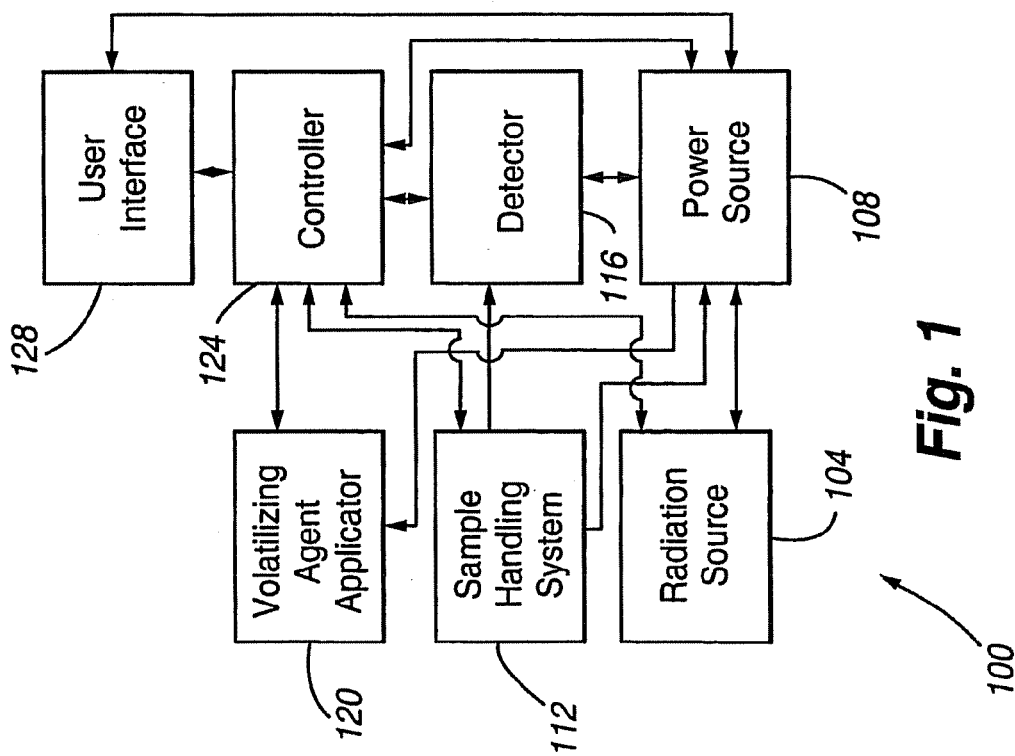

FIG. 2 illustrates a configuration of a portable detection system 200 employing the elements of FIG. 1. This device could be used, for example, to detect trace explosives associated with land mines or traces of explosives, chemical warfare agents, toxic industrial compounds or illicit drugs on the surfaces of luggage, people, cargo containers, and vehicles. The system 200 includes the detector 116, an on-board power source 108, and radiation source 104. The remaining elements of FIG. 1 are not specifically called out in FIG. 2. Additionally, the system 200 includes a handle 204, a sample collection housing 212, and an inlet 228 to the sample handling system 112. The sample collection housing 212 reflects emitted radiation towards the sample area 222 and provides sample containment and direction towards the inlet 228. The housing 212 interior is therefore reflective to the emitted wavelengths of radiation and impermeable to the fluids within the housing. The housing, of course, at least substantially surrounds the source 104. The inlet 228 typically includes an annular-shaped opening around the base of the source 104 or a plurality of discrete openings spaced at different positions adjacent to and around the base of the source 104.

In operation, the source 104 receives an energy pulse from the power source 108 and emits radiation 216. The surface particulates and condensable vapors 224 receive and absorb portions of the emitted radiation and either enter the vapor phase or otherwise become airborne. Simultaneously, the air within the housing 212 is heated. Due to the existence of a negative pressure within the housing 212 from the vacuum pump in the sample handling system 112, additional air 218 enters the area enclosed by the housing 212. The various airborne particulates, vapors and heated air are drawn through the vacuum inlet 228 and into the sample handling system 112. The sample handling system 112 transports the collected sample to the detector 116 for testing.

For optimal operation, it is desired that the radiation source 104 be located near the sample area 222. As will be appreciated, emitted radiation can rapidly dissipate in the air and be unable to impart sufficient energy to accurately sample the sample area 222. Preferably, the offset distance "$D_O$" from the lower edge 232 of the housing 212 and the lower edge 236 of the radiation source is no more than about 5 cm, and even more preferably ranges from about 1 to about 2 cm. Due to the negative pressure within the housing 212, it is preferred that either a space separate the lower edge 232 of the housing from the sample area surface 222 or that the lower edge 232 be in contact with the surface 222 but holes be provided in the periphery of the housing for air outside the housing 212 to enter into the area enclosed by the housing 212. If the suction is too great, loose debris, such as soil and small pebbles, can be sucked into the inlet and cause erroneous measurements or even damage the system 200. If too much air is drawn into the inlet, the entire plume will more likely be captured but the signal from the detector will be diluted. Preferably, the suction or negative pressure in the housing 212 should be sufficient to supply a flow rate of the sample of at least about 100 $cm^3$/minute and even more preferably from about 1.0 to about 5.0 liters per minute.

The dashed line 208 illustrates that the system 200 can have a remotely located power source 108. For some sources 104, such as a strobe, an on-board power source is often impractical. Accordingly, a power cord 208 can link the system 200 to the power source 108.

In another configuration shown in FIG. 11, the detection system includes a perforated surface, such as a screen, acting as a sample receiving surface. A person to be examined places his or her body part 1500, such as the hand, on the perforated surface 1504. The radiation 216 is emitted onto a surface 1508 of the body part 1500. The emitted radiation 216 causes any contaminated particulates and condensable vapors, which may include target or non-target substances, such as explosives or narcotics, to be lifted from the illuminated surface 1508 and passed into the inlet 228. The contaminated particulates and condensable vapors can be drawn into the inlet 228 by means of a vacuum as noted above and/or by means of a carrier gas blown at an angle onto the illuminated surface 1508 and/or onto the rear (non-illuminated) surface 1512 of the body part. The force of the carrier gas may be enough to transport the sample to the detector without a vacuum pump. The pressurized carrier gas may be blown onto and around the surfaces 1508 and/or 1512 of the body part during emission of radiation. The released particulates and vapors 1516 are carried into the inlet 228 and transported by the sample handling system to the detector.

In another configuration, the detection system is configured as a sampling wand to test the surfaces of inanimate objects, such as containers and vehicles, or of animate objects, such as a body part, for target or non-target substances.

Figure 3:
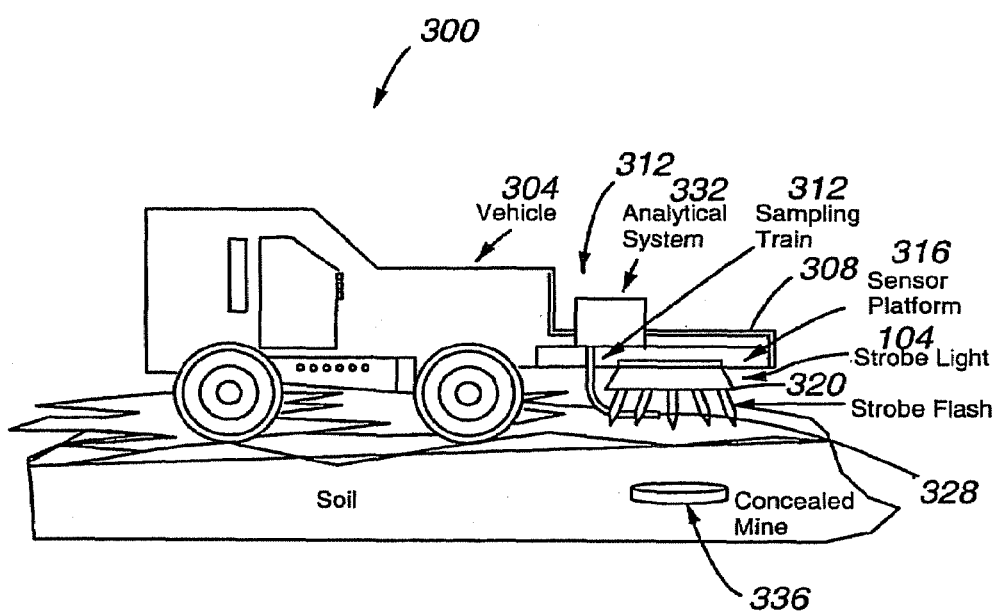

FIG. 3 depicts a mobile configuration of the detection system. The mobile detection system 300 includes a motorized (tracked or wheeled) vehicle 304 engaging a boom 308 mounted on the front of the vehicle. The detection system 312 is mounted on the boom via a detection platform 316. The system 312 includes a plurality of side-by-side radiation sources 104 surrounded by one or more housings 320. The sample handling system 112 includes one or more conduits 324 which has an inlet 328 in close proximity to one or more of the radiation sources to convey the samples to an analytical unit 332. The analytical unit includes the user interface 128, the controller 124, the detector 116, and portions of the sample handling system 112. The power source 108 may be the engine or generator of the vehicle. As the vehicle moves forward, the various radiation sources are illuminated substantially simultaneously to effect detection of the concealed mine 336. A sufficient number of radiation sources is provided to illuminate the ground for at least the width of the vehicle.

EXPERIMENTAL

EXAMPLE 1

Figure 6:
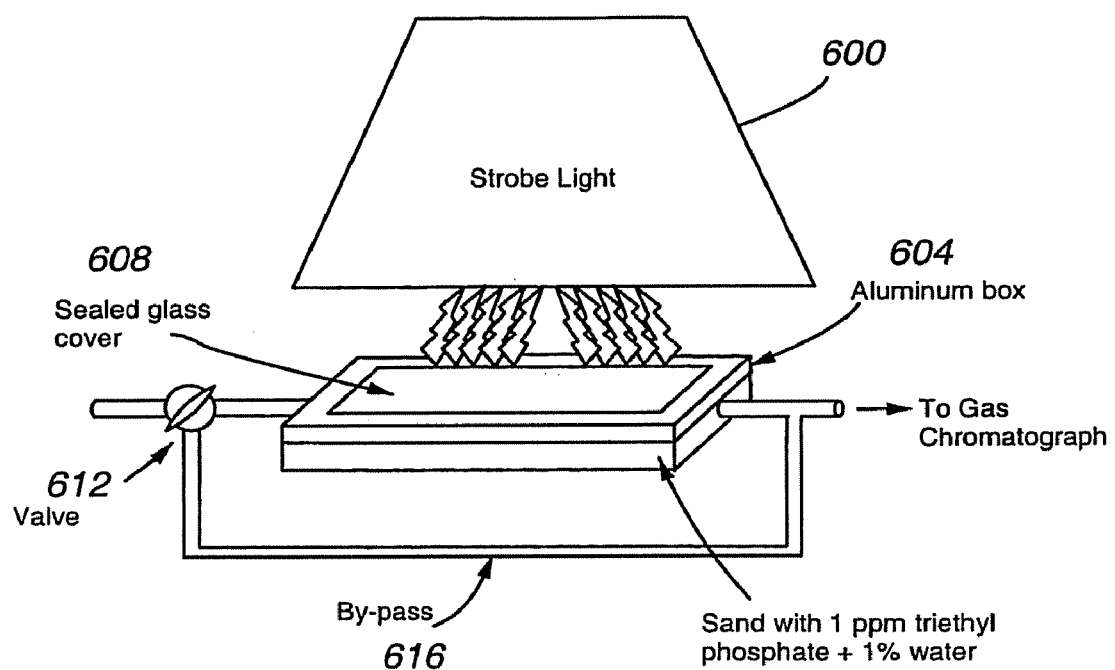

FIG. 6 depicts a test apparatus used in the first example. The apparatus includes a strobe light 600, an aluminum box 604 with a sealed glass cover 608 in which a sand sample is located. A valve 612 can select a bypass 616 or a passage through the sample to the gas chromatograph (not shown). The sand sample included 1 ppm of triethyl phosphate and 1% by weight water. Triethyl phosphate is a high boiling point material, having a boiling point of 215° C.

A stream of air, having a flow rate of 64 ml/minute, was passed through the by pass 616 and into the gas chromatograph with an open 3 mm stainless steel column and flame photometric detector fitted with a 526 nm optical filter for phosphorous detection. The baseline with the gas passing through the by pass was observed.

The gas flow was then switched to pass through the box and over the sand sample. There was no inflection in the baseline, indicating that the vapor pressure of the triethyl phosphate was too low to be detected. The detection limit for phosphorous is about $10^{-11}$ g/sec.

The strobe light 600 was then placed over the cell and flashed. The detector showed an immediate response as a large peak. The strobe light was a Speedotronic™ 2403™ strobe head with a Speedotronic™ Blackline™ power supply, delivering 2,400 watt-seconds of power. A strobe head of this size can generate a very large electrical disturbance and, to ensure that the detector was, in fact, responding to the phosphorus and not an electrical signal, the glass of the cell was covered with cardboard and the strobe was again fired. There was no response from the detector.

The cover was removed from the box and the strobe was again fired. There was another large response from the detector. The output of this experiment is presented in FIG. 7.

Figure 7:
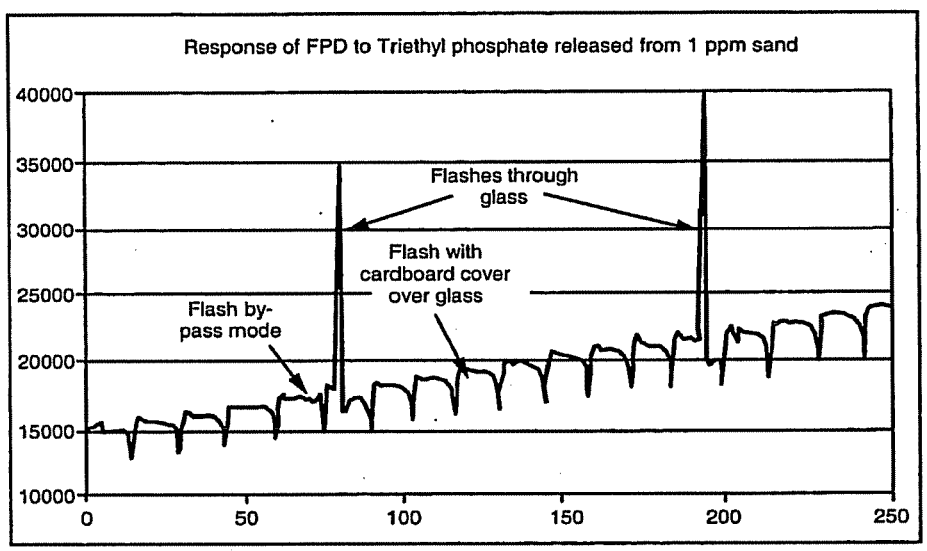

Referring to FIG. 7, the periodic signal from the detector is due to the thermal cycling of the heater in the detector.

This experiment shows that the test apparatus can successfully detect extremely low concentrations of a high boiling point substance.

EXAMPLE 2

Figure 8:
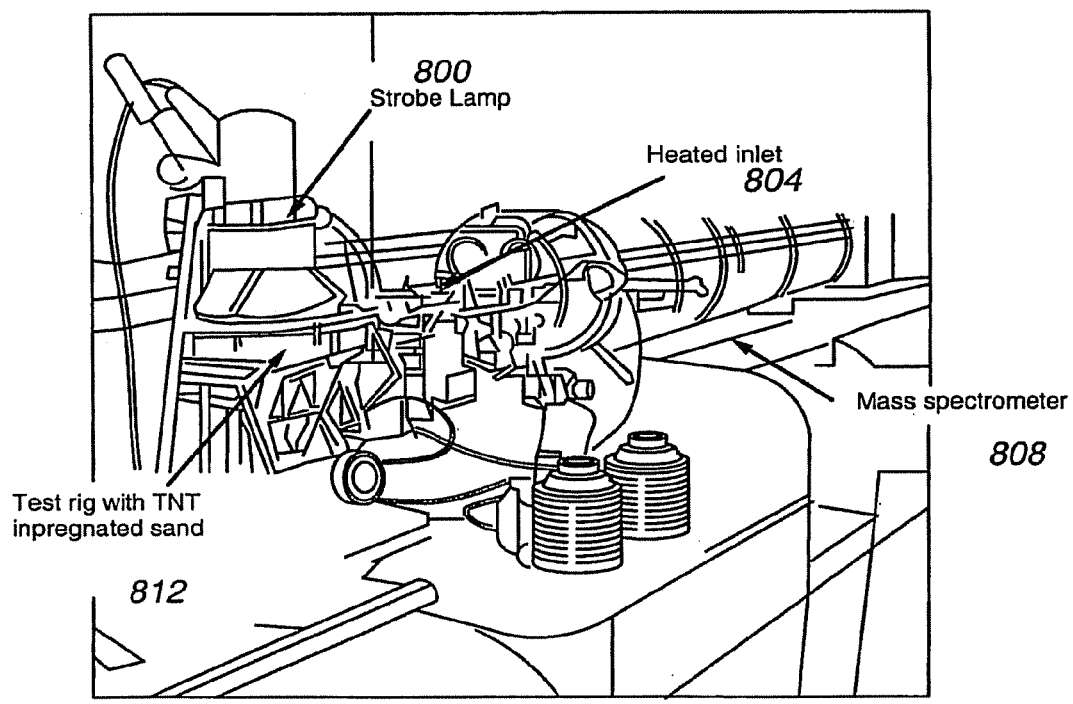

A second test apparatus is shown in FIG. 8. The apparatus includes a 1,200 Joule strobe lamp 800, a heated inlet 804, an atmospheric pressure chemical ionization tandem mass spectrometer 808, and a test rig 812 containing TNT impregnated sand. The test rig 812 was a cylindrical test cell with a glass cover that was configured similar to that of FIG. 6. Air was drawn through the apparatus and into the inlet system of the spectrometer. The spectrometer was set to monitor the response of the molecular ion of TNT at a mass to charge ratio (m/z) of 227.

Figure 9:
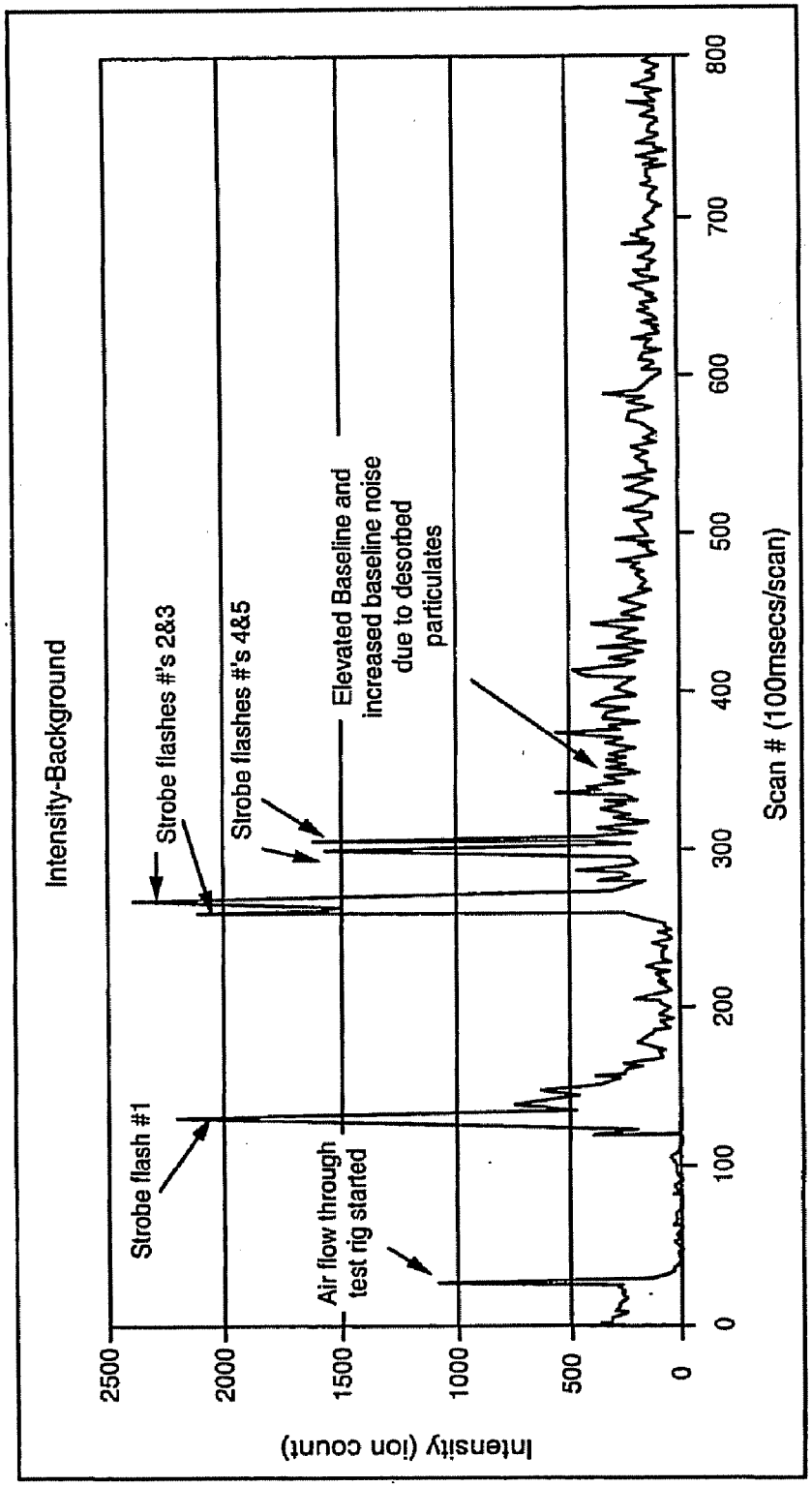

The results of one of these experiments are presented in FIG. 9. The mass chromatogram of FIG. 9 illustrates the release of a series of sharply defined plumes of vapor in response to the influx of energy from the strobe. It is also apparent that the baseline after the first strobe flash becomes elevated and analytically much noisier. It is assumed that this increase in the baseline activity is due to explosive carrying particulate material that has been released from the soil by the strobe. This activity increases with the subsequent flashes due to the sand being dried by the heat of the strobe and becoming more prone to release fine particulates.

EXAMPLE 3

The test rig of FIG. 8 was used. Sand samples were impregnated with explosives and explosive related compounds, using dilute solutions in acetone. The concentrations were 4, 10, 25, 125, and 1,250 ppb. The solvent was removed by evaporation at room temperature. One percent water was added to each sand sample, which was then stored in the dark in a glass jar. For the tests, the sand was placed in the metal base, and the glass cover attached.

The test rig 812 containing the impregnated sand was attached to the mass spectrometer 808 via a heated glass inlet 804. Room air was drawn over the sand using the sampling pump of the mass spectrometer. The sampling rate was high (several liters per minute). The strobe light used a 15 cm diameter shade and was positioned directly above the glass of the test rig.

The mass spectrometer was set to monitor the response of the molecular ion of TNT at a mass to charge ratio (m/z) of 227. The initial test used a relatively high concentration of 1.25 ppm TNT on sand to aide in the optimization of the sample transfer area and the mass spectrometer response. The strobe flash came from a 1,200 watt-second (joules) Speedotron™ Blackline 2403™ power pack and single strobe head.

Figure 10:
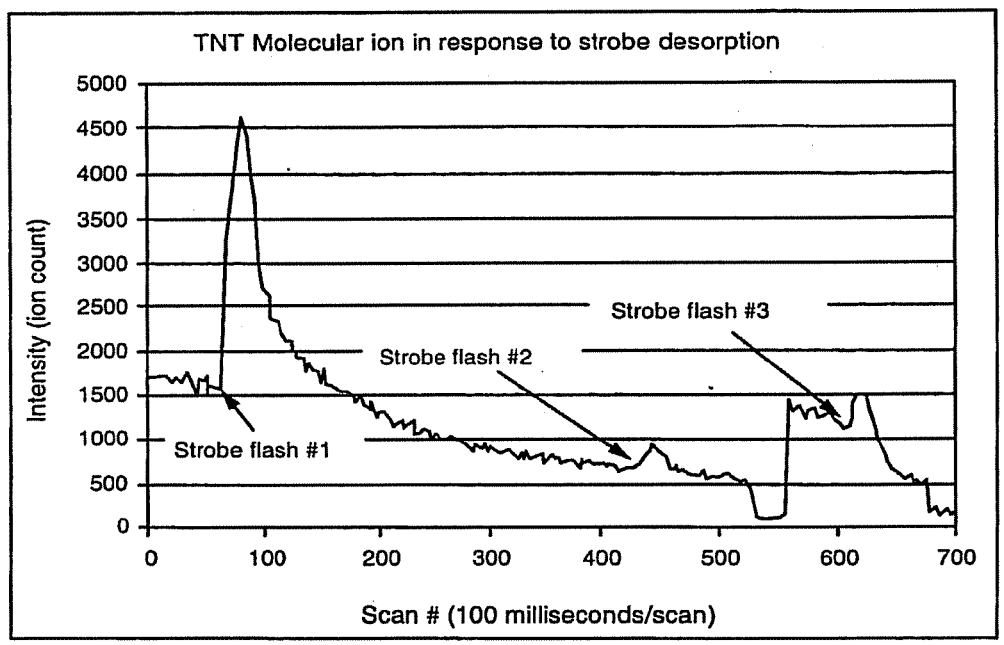
Figure 11:
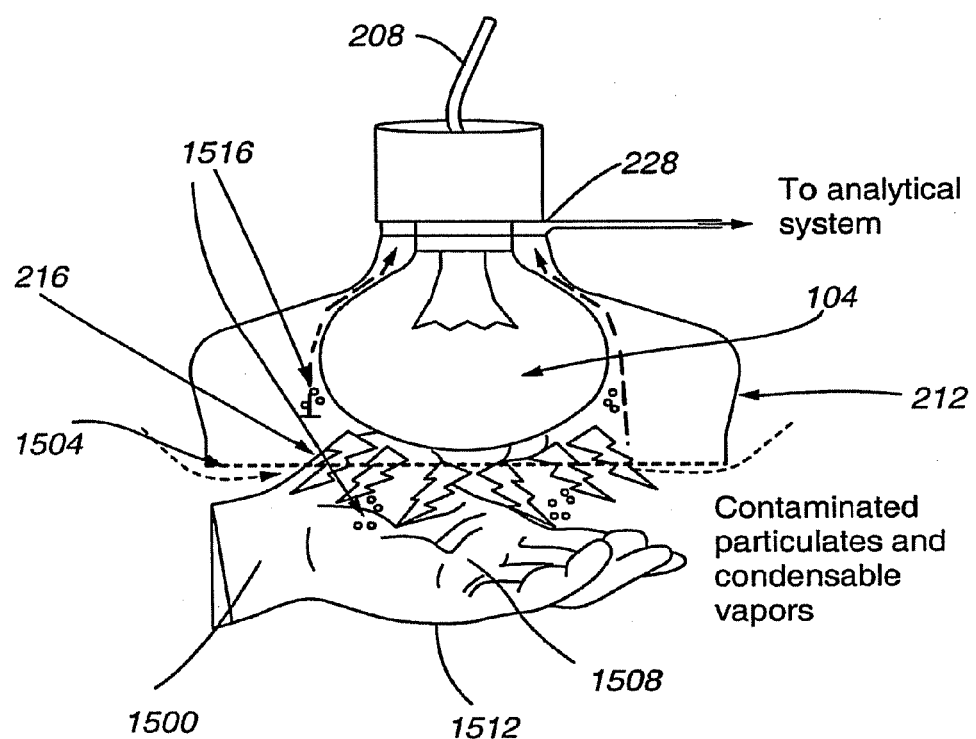

FIG. 10 depicts a typical response to the flash of the strobe lamp. As can be seen from FIG. 10, there was an immediate, high signal-to-noise ratio strong response to the first strobe flash. The signal rose quickly to a maximum but declined back to the baseline more slowly. This is believed to be due to the initial plume of material being released from the sand by the strobe flash, followed by a slowly declining enhanced background due to the generalized heating from 5,000 calories that were delivered to the surface of the sand by the strobe.

The peaks associated with later flashes (nos. 2 and 3) are much smaller due, perhaps, either to drying of the sand by the first strobe flash or the stripping of the available TNT from the surfaces exposed to the strobe. The potential influence of the water in amplifying the response could be due to the moisture interceding between the explosive and the mineral surface, thus weakening the binding and/or to a plume of water vapor facilitating the transfer of TNT through the sample inlet. The areas under the peaks were quantified after correction for the background and the sloping baseline, using the calibration constant from the earlier calibration work. The quantified results are shown in Table I.

|  | Area | Concentration of TNT (ng) |
| --- | --- | --- |
| Integrated Peak Area Flash # 1 = | 62,299 | 13.67 |
| Integrated Peak Area Flash # 2 = | 2,336 | 0.51 |
| Integrated Peak Area Flash # 3 = | 2,593 | 0.57 |

The quantified data in Table I demonstrate the power of the underlying concept, i.e., that a high-powered strobe is capable of creating readily detectable plumes of TNT from trace quantities of the explosive on a sand substrate. Furthermore, the amounts released from the sand ($1.5 \times 10^{-8}$ to $5 \times 10^{-10}$ g) are well within the analytical range of a variety of explosive sensors.

Figure 12:
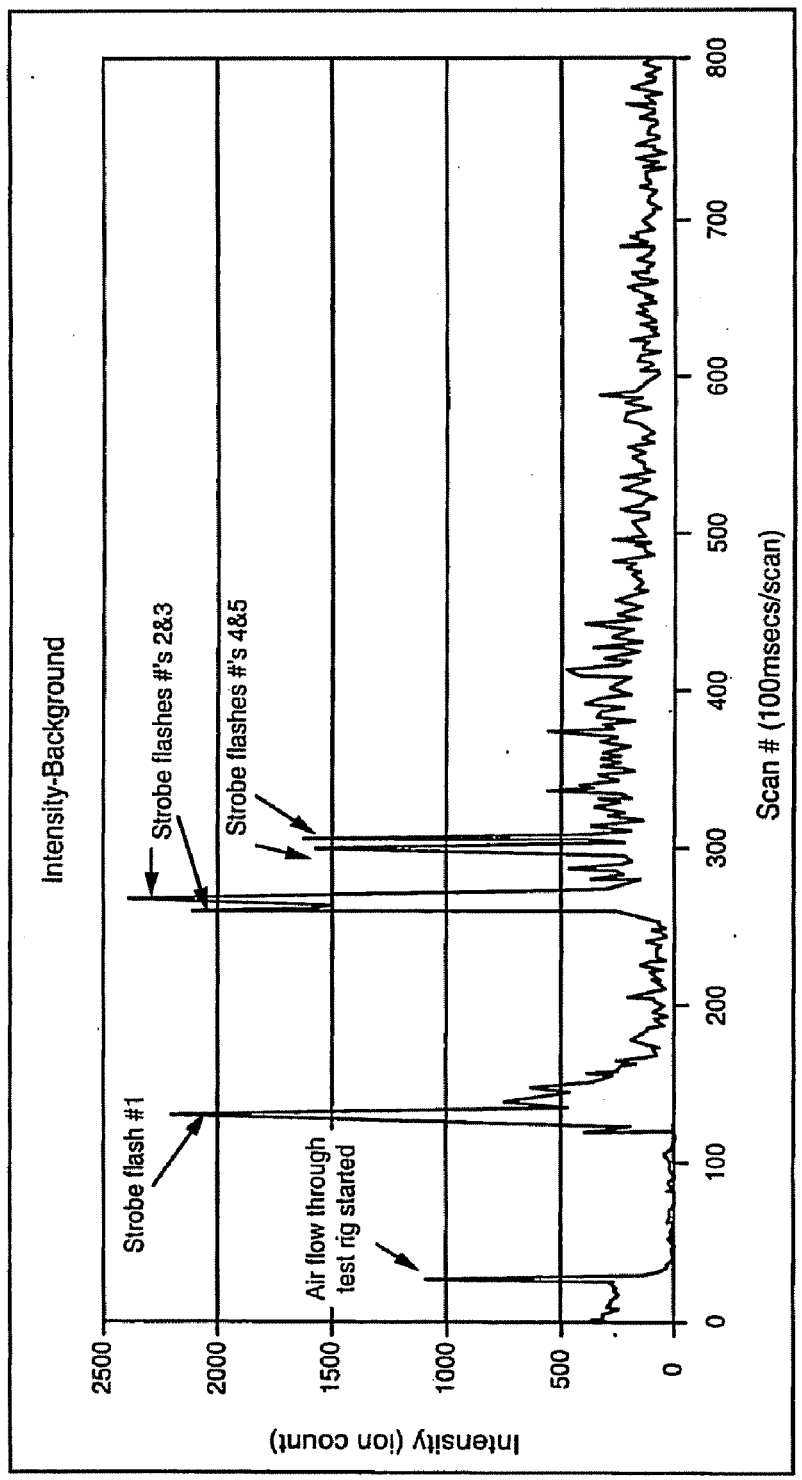

To test the effects of increased water content of the sand, the sample was removed from the test apparatus and an additional 2% water added. The sand was mixed and returned to the test rig and again subjected to the flash of the strobe lamp. The results of these tests are shown in FIG. 12 and Table II below.

|  | Peak Area | Concentration of TNT (ng) |
| --- | --- | --- |
| Peak # 1 = | 15,601 | 3.4 |
| Peak # 2 & 3 = | 12,031 | 2.6 |
| Peak # 4 = | 2,853 | 0.6 |
| Peak # 5 | 1,718 | 0.4 |

The first peak shows a similar pattern to the earlier test, with a sharp rise in the TNT concentration immediately after the flash, with a sloping return to the baseline. It is important to note that the very low baseline prior to the first strobe flash indicates that the TNT on the soil was not detected by this sophisticated and sensitive instrument, despite the fact that the air was being drawn over sand carrying 1,250 ppb TNT and directly into the mass spectrometer.

In addition to the immediate sharp peaks in response to each of the flashes, the baseline becomes elevated and nosier, particularly for Peak No. 5. This, perhaps, is due to particulates, which were released by the strobe flash and collected in the heated inlet system where they continued to release TNT for several tens of seconds.

In this test, all of the later flashes gave a very sharp response with a rapid return to base line. The later flashes gave a smaller response than the first flash. The fourth and fifth flashes had a similar actual concentration of TNT as the later flashes in the first test (FIG. 10) but the character of the response was markedly different, with the peaks being sharp and very well-defined.

These data clearly indicate that the presence of water can have a dramatic impact on the response.

Figure 13:
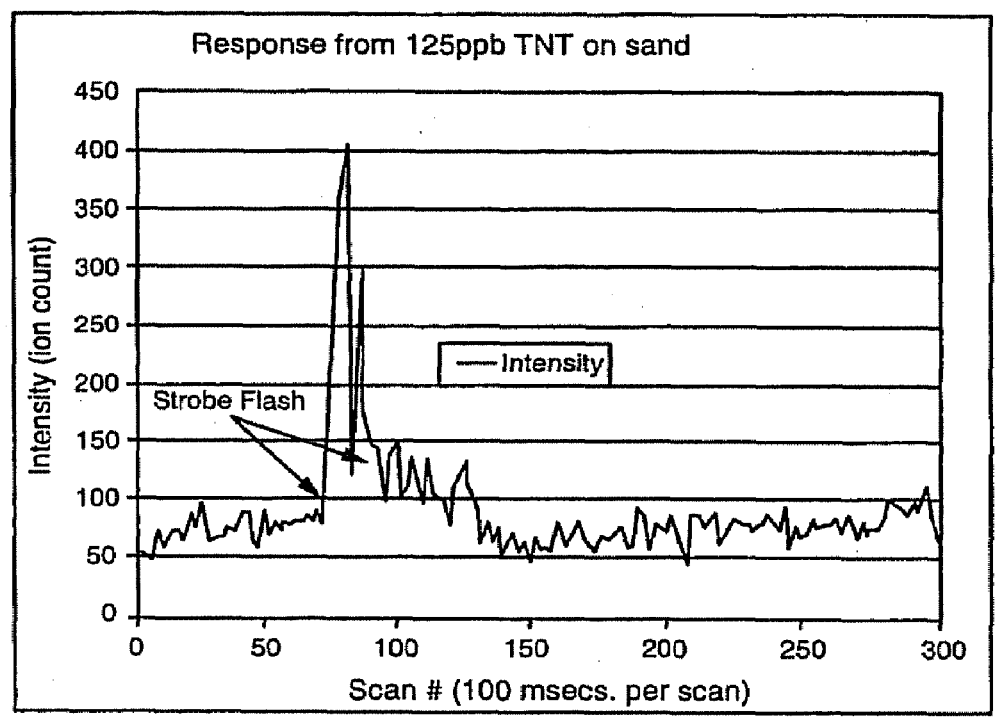

To test the influence of decreasing the concentration of TNT on the sand a further test was conducted with 125 ppb TNT on sand with 1% water. The result is shown in FIG. 13. The sharply defined peak had an integrated area equivalent to 0.44 ng of TNT.

EXAMPLE 4

Figure 14:
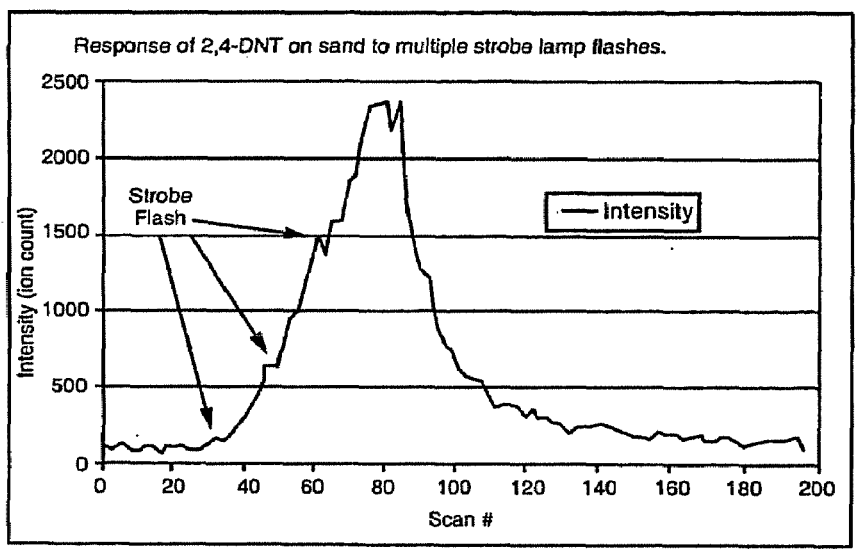

A test was conducted with the test rig of FIG. 8 using 2,4-dinitrotoluene. The results are shown in FIG. 14.

While the test was performed, the DNT appeared to be breaking down. Whether this was due to photoylsis by the strobe lamp or the corona discharge in the ionization area of the mass spectrometer is not clear. It was found that DNT gave ions at m/z 92 (toluene), m/z 137 (nitrotoluene), and m/z 137 (DNT). The need to monitor several ions reduced the sensitivity of the analysis and increased the baseline noise. However, a single test with 1.25 ppm DNT on sand gave a strong peak in response to several flashes from the strobe.

Although the DNT response was strong, it was not as sharp as the response from TNT. It is possible that the response is due to the generalized heating of the more volatile DNT on the soil rather than to rapid desorption.

Significant observations from these tests include the following:

(i) Plumes containing nanogram quantities of TNT were released by the use of a strobe flash from the surface of TNT-spiked sand. This represented a 100 to 1,000 fold increase over the equilibrium TNT concentration.

(ii) TNT binds aggressively to all available surfaces and will require careful transfer line design. A stainless steel tube was replaced by a short, heated glass interface when a direct injection of a 200 ng plume of TNT vapor from the heated calibration test rig failed to elicit any response from the mass spectrometer. This new arrangement immediately led to strong, reproducible plumes of TNT vapor in response to injections of standard solutions of TNT into the apparatus.

(iii) Other explosive related chemicals may be expected to behave in a similar or more advantageous manner, effectively amplifying the signature by active sampling.

(iv) Moisture appears to help liberate the TNT under the impact of the strobe.

(v) It appears that the strobe releases both vapors and explosive-bearing particulates so a detection system may need to utilize a heated filter.

A number of variations and modifications of the invention can be used. It would be possible to provide for some features of the invention without providing others. For example in one alternative embodiment, the system is used to detect low boiling point or high vapor pressure materials. In another alternative embodiment, multiple detectors can be used simultaneously or near simultaneously to detect different target substances.

The present invention, in various embodiments, includes components, methods, processes, systems and/or apparatus substantially as depicted and described herein, including various embodiments, subcombinations, and subsets thereof Those of skill in the art will understand how to make and use the present invention after understanding the present disclosure. The present invention, in various embodiments, includes providing devices and processes in the absence of items not depicted and/or described herein or in various embodiments hereof, including in the absence of such items as may have been used in previous devices or processes, e.g., for improving performance, achieving ease and\or reducing cost of implementation.

The foregoing discussion of the invention has been presented for purposes of illustration and description. The foregoing is not intended to limit the invention to the form or forms disclosed herein. In the foregoing Detailed Description for example, various features of the invention are grouped together in one or more embodiments for the purpose of streamlining the disclosure. This method of disclosure is not to be interpreted as reflecting an intention that the claimed invention requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the invention.

Moreover though the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for detecting a high boiling point and/or a low vapor pressure material, comprising:
   providing a housing comprising an inlet, a strobe, a gas source, and a detector, wherein the housing at least substantially surrounds the strobe and the inlet and wherein the inlet is positioned between the strobe and a surface potentially comprising a high boiling point and/or low vapor pressure material;
   directing radiation from the strobe onto the surface to volatilize the high boiling point and/or low vapor pressure material, the directing radiation step is conducted over a time period of no more than about $\frac{1}{100}^{th}$ seconds;
   transporting an airborne sample comprising at least a portion of any volatilized high boiling point and/or low vapor pressure materials on the surface through the inlet and through a heated conduit to the detector, wherein an internal surface of the heated conduit is maintained at a temperature sufficient to inhibit absorption and/or condensation of the high boiling point and/or low vapor pressure material on the internal surface, and wherein the heated conduit extends from the inlet to the detector; and
   detecting whether or not the high boiling point and/or low vapor pressure material is present in the collected sample.

2. The method of claim 1, wherein said transporting further comprises directing a pressurized stream of gas from the gas source onto and/or around said surface at a flow rate sufficient to transport the gaseous stream and any high boiling point and/or low vapor pressure materials on the surface upward through the inlet of the housing and through the heated conduit after contact of the gaseous stream with the surface.

3. The method of claim 1, wherein said transporting step further comprises maintaining a negative pressure in the vicinity of the surface to draw said sample through the inlet of the housing and through the heated conduit.

4. The method of claim 1, wherein the temperature of the heated conduit ranges from about 100° C. to about 250° C., and wherein the temperature of the heated conduit is at least the condensation temperature of the material.

5. The method of claim 1, wherein the strobe comprises a xenon flash tube, and wherein said directing radiation step further comprises directing at least about 200 Joules of cumulative energy onto the surface.

6. The method of claim 1, wherein the high boiling point and/or low vapor pressure material is at least one of an explosive, an explosive related compound, a chemical warfare agent, a drug, a toxic industrial compound, and derivatives thereof, and wherein the radiation has one or more wavelengths in the range of from about 300 nm to about 700 nm in the visible region and/or from about 700 nm to about 2 microns in the infrared region of the electromagnetic spectrum.

7. The method of claim 1, wherein an offset distance between a surface of the strobe and the surface is no more than about 5 cm.

8. The method of claim 1, further comprising before the directing radiation step:
   applying a volatilizing agent to the surface, wherein the volatilizing agent is at least one of water, a volatile organic solvent, and mixtures thereof;
   wherein the strobe has an outputted energy profile, and wherein a peak of the profile is located in a radiation absorption band of the volatilizing agent.

9. The method of claim 1, wherein the strobe has an outputted energy profile, and wherein a peak of the profile is located in a radiation absorption band of the material.

10. A system for detecting a high boiling point and/or a low vapor pressure material, comprising:
    a strobe operable to direct radiation onto a surface potentially comprising a high boiling point and/or low vapor pressure material over a time period of no more than about $\frac{1}{100}$th seconds to volatilize the high boiling point and/or low vapor pressure material;
    a housing at least substantially surrounding the strobe and an inlet to the housing, said housing comprising a sample handling system operable to collect an airborne sample comprising at least a portion of any volatilized high boiling point and/or low vapor pressure materials at and/or near the surface; and
    a detector operable to detect whether or not the high boiling point and/or low vapor pressure material is present in the collected sample;
    wherein said sample handling system comprises a heated conduit extending substantially from the inlet to the detector and a means for transporting said collected airborne sample through said heated conduit to said detector, wherein an internal surface of the heated conduit is maintained at a temperature sufficient to inhibit absorption and/or condensation of the high boiling point and/or low vapor pressure material on the internal surface.

11. The system of claim 10, further comprising a gas source for directing a stream of pressurized gas onto the surface at a flow rate sufficient to transport the gaseous stream and any high boiling point and/or low vapor pressure materials on said surface upward through the inlet of the housing and through the heated conduit after contact of the gaseous stream with the surface.

12. The system of claim 10, wherein the sample handling system further comprises a vacuum pump to maintain a negative pressure in the vicinity of the surface.

13. The system of claim 10, wherein the temperature of the heated conduit ranges from about 100° C. to about 250° C., and wherein the temperature of the heated conduit is at least the condensation temperature of the material.

14. The system of claim 10, wherein the strobe comprises a xenon flash tube wherein the high boiling point and/or low vapor pressure material is at least one of an explosive, an explosive related compound, a chemical warfare agent, a drug, a toxic industrial compound, and derivatives thereof, and wherein the radiation has one or more wavelengths in the range of from about 300 nm to about 700 nm in the visible region and/or from about 700 nm to about 2 microns in the infrared region of the electromagnetic spectrum.

15. The system of claim 10, further comprising an applicator operable to apply a volatilizing agent to the surface before radiation is contacted with the surface;
wherein the strobe has an outputted energy profile, and wherein a peak of the profile is located in a radiation absorption band of the volatilizing agent.

16. A system for detecting a high boiling point and/or a low vapor pressure material, comprising:
a strobe operable to direct radiation onto a surface potentially comprising a high boiling point and/or low vapor pressure material to volatilize the high boiling point and/or low vapor pressure material, wherein radiation emission cycles of the strobe are repeated at a frequency of at least about 0.2 Hz;
a housing at least substantially surrounding the strobe and an inlet to the housing, said housing comprising a sample handling system operable to collect an airborne sample comprising at least a portion of any volatilized high boiling point and/or low vapor pressure materials at and/or near the surface; and
a detector operable to detect whether or not the high boiling point and/or low vapor pressure material is present in the collected sample;
wherein said sample handling system comprises a heated conduit extending substantially from the inlet to the detector and a means for transporting said collected airborne sample through said heated conduit to said detector, wherein an internal surface of the heated conduit is maintained at a temperature sufficient to inhibit absorption and/or condensation of the high boiling point and/or low vapor pressure material on the internal surface.

17. The system of claim 16, further comprising a gas source for directing a stream of pressurized gas onto the surface at a flow rate sufficient to transport the gaseous stream and any high boiling point and/or low vapor pressure materials on said surface upward through the inlet of the housing and through the heated conduit after contact of the gaseous stream with the surface.

18. The system of claim 16, wherein the sample handling system further comprises a vacuum pump to maintain a negative pressure in the vicinity of the surface.

19. The system of claim 16, wherein the temperature of the heated conduit ranges from about 100° C. to about 250° C., and wherein the temperature of the heated conduit is at least the condensation temperature of the material.

20. The system of claim 16, wherein the heated conduit comprises a glass and/or ceramic surface adjacent the transported sample, and wherein the heated conduit comprises a silanizing agent.

21. The method system of claim 16, wherein the heated conduit comprises an at least substantially nonpolar surface adjacent the transported sample.

22. The system of claim 16, wherein the strobe comprises a xenon flash tube wherein the high boiling point and/or low vapor pressure material is at least one of an explosive, an explosive related compound, a chemical warfare agent, a drug, a toxic industrial compound, and derivatives thereof, and wherein the radiation has one or more wavelengths in the range of from about 300 nm to about 700 nm in the visible region and/or from about 700 nm to about 2 microns in the infrared region of the electromagnetic spectrum.

* * * * *